(12) United States Patent
Song et al.

(10) Patent No.: US 8,748,592 B1
(45) Date of Patent: Jun. 10, 2014

(54) SIRNA FOR INHIBITION OF OTUB1 EXPRESSION AND PHARMACEUTICAL COMPOSITION CONTAINING THE SAME

(71) Applicant: Korea Institute of Science and Technology, Seoul (KR)

(72) Inventors: Eun Joo Song, Seoul (KR); Hyunjung Lee, Seoul (KR)

(73) Assignee: Korean Institute of Science and Technology, Seoul (KR)

( * ) Notice: Subject to any disclaimer, the term of this patent is extended or adjusted under 35 U.S.C. 154(b) by 0 days.

(21) Appl. No.: 13/760,271

(22) Filed: Feb. 6, 2013

(30) Foreign Application Priority Data

Jan. 17, 2013 (KR) .................. 10-2013-0005431

(51) Int. Cl.
- *C07H 21/04* (2006.01)
- *A61K 48/00* (2006.01)
- *C12N 15/113* (2010.01)

(52) U.S. Cl.
CPC ............ *C12N 15/113* (2013.01); *A61K 48/00* (2013.01)
USPC ...................................... 536/24.5; 514/44 R

(58) Field of Classification Search
None
See application file for complete search history.

(56) References Cited

U.S. PATENT DOCUMENTS 7,691,997 B2 * 4/2010 Khvorova et al. ........... 536/24.5

OTHER PUBLICATIONS

Frank Stegmeier et al., "Anaphase initiation is regulated by antagonistic ubiquitination and deubiquitination activities", Nature, vol. 446, Apr. 19, 2007, pp. 876-881.
Sebastian Nijman et al., "The Deubiquitinating Enzyme USP1 Regulates the Fanconi Anemia Pathway", Molecular Cell, vol. 17, Feb. 4, 2005, pp. 331-339.
Tony Huang et al., "Regulation of monoubiquitinated PCNA by DUB autocleavage", Nature Cell Biology, vol. 8, No. 4, Apr. 2006, pp. 339-347.
CL Brooks et al., "The p53-Mdm2-HAUSP complex is involved in p53 stabilization by HAUSP", Oncogene, vol. 26, 2007, pp. 7262-7266.
Heui-Yun Joo et al., "Regulation of cell cycle progression and gene expression by H2A deubiquitination", Nature, vol. 449, Oct. 25, 2007, pp. 1068-1073.
Shinichiro Nakada et al., "Non-canonical inhibition of DNA damage-dependent ubiquitination by OTUB1", vol. 466, Aug. 19, 2010, pp. 941-948.
Yu-Chi Juang et al., "OTUB1 Co-opts Lys48-Linked Ubiquitin Recognition to suppress E2 Enzyme Function", Molecular Cell, vol. 46, May 25, 2012, pp. 549.

* cited by examiner

*Primary Examiner* — Tracy Vivlemore
*Assistant Examiner* — Kate Poliakova-Georgantas
(74) *Attorney, Agent, or Firm* — Staas & Halsey LLP

(57) ABSTRACT

The present invention relates to an siRNA inhibiting expression of the OTUB1 protein and a composition for preventing or treating cancer containing same as an active ingredient. In accordance with the present invention, cancer cell growth can be remarkably inhibited by inhibiting OTUB1 expression using the siRNA of the present invention.

3 Claims, 9 Drawing Sheets

H358

SIRNA FOR INHIBITION OF OTUB1 EXPRESSION AND PHARMACEUTICAL COMPOSITION CONTAINING THE SAME

CROSS-REFERENCE TO RELATED APPLICATIONS

This application claims priority under 35 U.S.C. §119 to Korean Patent Application No. 10-2013-0005431, filed on Jan. 17, 2013, in the Korean Intellectual Property Office, the disclosure of which is incorporated herein by reference in its entirety.

BACKGROUND (a) Technical Field

The present invention relates to an siRNA inhibiting expression of OTUB1 and a pharmaceutical composition containing same.

(b) Background Art

Division, growth, differentiation and necrosis of cells are regulated by complicated processes and abnormality of these processes leads to cancer owing to unregulated cell proliferation. In particular, abnormality of cell division is thought as the direct cause of cancer and substances that regulate cell division are considered as targets for prevention and treatment of cancer.

Cell division occurs during the cell cycle consisting of $G_1$, S, $G_2$ and M phases. A checkpoint exists in each phase and regulates the progress of the cell cycle. The activity of the proteins involved in the regulation of the cell cycle is mainly controlled through phosphorylation by kinases and degradation by ubiquitination.

Together with ubiquitination, deubiquitination also plays an important role in the regulation of cell division. Usp44 regulates anaphase initiation by deubiquitinating cdc20 (Stegmeier F, Rape M, Draviam V M, et al. Anaphase initiation is regulated by antagonistic ubiquitination and deubiquitination activities. *Nature* 2007; 446: 87681) and Usp1 and Usp7 are known to regulate DNA damage checkpoint (Nijman S M, Huang T T, Dirac A M, et al. The deubiquitinating enzyme USP1 regulates the Fanconi anemia pathway. *Mol Cell* 2005; 17: 3319, Huang T T, Nijman S M, Mirchandani K D, et al. Regulation of monoubiquitinated PCNA by DUB autocleavage. *Nat Cell Biol* 2006; 8: 33947). Also, Usp7 is known to regulate stabilization of p53 by deubiquitinating Mdm2 (Brooks C L, Li M, Hu M, Shi Y, Gu W. The p53-Mdm2-HAUSP complex is involved in p53 stabilization by HAUSP. *Oncogene* 2007; 26: 72626) and Usp16 is known to regulate chromosomal segregation during mitosis by deubiquitinating histone H2A (Joo H Y, Zhai L, Yang C, et al. Regulation of cell cycle progression and gene expression by H2A deubiquitination. *Nature* 2007; 449: 106872).

Ovarian tumor domain-containing proteases (OTUs) are one of deubiquitinating enzyme families. The OTU family includes OTUB1, OTUB2, A20, etc. and shares the OTU domain consisting of 130 amino acids. OTUB1 is the first known member of the OTU family proteins and is known to be uniformly distributed in all tissues. Unlike other deubiquitinating enzymes, OTUB1 is reported to inhibit DNA damage in a non-catalytic manner by binding to the E2 enzyme UBC13 rather than directly deubiquitinating its substrate (Nakada S, Tai I, Panier S, Al-Hakim A, Iemura S, Juang Y C, O'Donnell L, Kumakubo A, Munro M, Sicheri F, Gingras A C, Natsume T, Suda T, Durocher D. Non-canonical inhibition of DNA damage-dependent ubiquitination by OTUB1. *Nature* 2010 Aug. 19; 466 (7309): 941-6). It is also reported to regulate deubiquitinating enzymes by binding to UbcH5, UBE2D and UBE2E (Juang Y C, Landry M C, Sanches M, Vittal V, Leung C C, Ceccarelli D F, Mateo A R, Pruneda J N, Mao D Y, Szilard R K, Orlicky S, Munro M, Brzovic P S, Klevit R E, Sicheri F, Durocher D. OTUB1 co-opts Lys48-linked ubiquitin recognition to suppress E2 enzyme function. *Mol Cell* 2012 Feb. 10; 45 (3): 384-97). As such, although researches on the function of OTUB1 are reported recently, there are few reports on its direct relationship with cancer.

The inventors of the present invention have found that the expression of the OTUB1 protein is remarkably increased in lung cancer cells when compared to in normal lung cells and inhibition of OTUB1 in the lung cancer cells with siRNA leads to inhibited cell growth.

Throughout the specification, a number of publications and patent documents are referred to and cited. The disclosure of the cited publications and patent documents is incorporated herein by reference in its entirety to more clearly describe the state of the related art and the present invention.

SUMMARY

The inventors of the present invention have researched for substances that regulate cell division associated with abnormal cell proliferation and found that overexpression of OTUB1, a member of the OTU family, is directly related with cancer growth and that cancer cell growth is remarkably inhibited when the OTUB1 overexpression is inhibited by siRNA.

The present invention is directed to providing an siRNA inhibiting expression of the OTUB1 protein.

The present invention is also directed to providing a composition for preventing or treating cancer containing the siRNA as an active ingredient.

Other features and aspects of the present invention will be apparent from the following detailed description, drawings and claims.

BRIEF DESCRIPTION OF THE DRAWINGS

The above and other objects, features and advantages of the present invention will now be described in detail with reference to certain exemplary embodiments thereof illustrated in the accompanying drawings which are given hereinbelow by way of illustration only, and thus are not limitative of the invention, and wherein.

DETAILED DESCRIPTION

Figure 1:
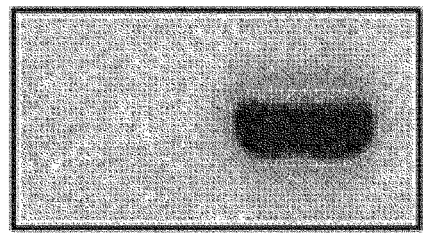
FIG. 1 shows overexpression of the OTUB1 protein in NCI-H358 non-small-cell lung cancer cells as compared to in WI38 normal lung cells.
Figure 1:
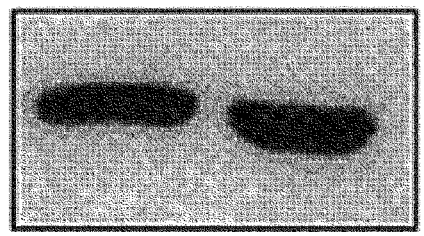

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

In an aspect, the present invention provides an siRNA inhibiting expression of the OTUB1 protein.

OTUB1 is a member of the ovarian tumor domain-containing protease (OTU) family proteins, which are deubiquitinating enzymes. It is uniformly distributed in all tissues and regulates deubiquitinating enzymes by binding to UBC13, UbcH5, UBE2D, UBE2E, etc. rather than directly deubiquitinating its substrate. The inventors of the present invention have found that OTUB1 is overexpressed in cancer cells as compared to in normal cells and that cancer cell growth can be remarkably inhibited by inhibiting its expression.

In the present invention, OTUB1 is meant to include its variant whose activity is not decreased. Specifically, it includes one having an amino acid sequence of SEQ ID NO 1.

In the present invention, the phrase "inhibition of expression" means a reduction or decrease of the level of mRNAs and/or proteins produced from a target gene, via RNA interference (RNAi) in which mRNA is cleaved.

An siRNA may be directly synthesized in a test tube and then introduced into a cell through transfection. Alternatively, an siRNA expression vector or a PCR-derived siRNA expression cassette designed to express an siRNA in a cell may be transfected or infected into a cell. The method for preparing the siRNA and introducing it into a cell or an animal may be determined differently depending on the particular purpose and the biological functions of the target gene product.

In the present invention, the term "siRNA" refers to an RNA molecule capable of mediating RNA interference or gene silencing. The siRNA molecule used in the present invention includes a sequence complementary to that of the OTUB1 mRNA. The term "complementary" includes not only 100% complementarity but also incomplete complementarity capable of inhibiting expression of the OTUB1 gene via RNA interference. It includes 90% complementarity, more specifically 98% complementarity, most specifically 100% complementarity. Specifically, the full length of the OTUB1 siRNA may be 10-60 nucleotides, more specifically 15-30 nucleotides.

In a specific embodiment of the present invention, the siRNA of the present invention has a nucleotide sequence complementary in part to the sequence of the OTUB1 mRNA of SEQ ID NO 1. The matched part of the sequence may have a length effective for mediating gene silencing of OTUB1, i.e. at least 10 nucleotides (nt), specifically at least 15 nt.

The siRNA molecule of the present invention includes the minimum length of sequence or a sequence complementary thereto and may be specifically at most 60 nt, more specifically at most 30 nt, in length.

In a specific embodiment of the present invention, the siRNA molecule of the present invention includes a sense sequence of SEQ ID NO 2 or SEQ ID NO 4 and an antisense sequence of SEQ ID NO 3 or SEQ ID NO 5.

The terminal structure of the siRNA may be either blunt or cohesive as long as the expression of the target gene can be inhibited by RNAi. Either the 3'-terminal or the 5'-terminal may be cohesive (overhanging). The number of overhanging nucleotides is not limited. For example, 1-8 nucleotides, specifically 2-6 nucleotides, may be overhanging. As long as the siRNA maintains its effect of inhibiting the expression of the target gene, it may contain a low-molecular-weight RNA (which may be a natural RNA molecule such as tRNA, rRNA or viral RNA or an artificial RNA molecule), for example, in the overhanging portion of one end. The terminal structure of the siRNA is not necessarily cut-off at both ends. The siRNA may have a stem-loop structure in which both ends of a double-stranded RNA are connected by a linker RNA. The length of the linker is not particularly limited as long as the pairing of the stem portion is not hindered.

The siRNA of the present invention includes a variant, or a functional equivalent, with one or more substitution, insertion, deletion or a combination thereof without changing its activity. The variant may have at least 70%, specifically at least 80%, more specifically at least 90%, most specifically at least 95%, of identity with the above-descried sequences of siRNA (SEQ ID NOS 2-5). The identity may be easily determined by comparing a polynucleotide sequence with that of the matching portion of a target polynucleotide using a computer algorithm widely known in the art, e.g. Align or BLAST (Altschul, S. F. *J. Mol. Biol.* 219, 555-565, 1991; Henikoff, S. and Henikoff, J. G. *Proc. Natl. Acad. Sci. USA* 89, 10915-10919, 1992).

The siRNA of the present invention may be used for inhibition of expression in any cells in which the OTUB1 protein is expressed. Specifically, it may be used to inhibit cancer cell growth.

In another aspect, the present invention provides a pharmaceutical composition containing an siRNA inhibiting expression of OTUB1 in a cell by complementary binding to a transcript sequence of the OTUB1 protein as an active ingredient.

The siRNA of the present invention is administered as a pharmaceutical composition for preventing or treating cancer. The administration may be achieved by a known method in which the siRNA is introduced into a desired target cell in vitro or in vivo. The method for introducing the siRNA into the cell is not particularly limited. For example, the siRNA may be directly incorporated into a host cell or the cell may be transfected with a recombinant vector expressing the siRNA. The recombinant vector expressing the siRNA may be a plasmid or a viral vector selected from a group consisting of adeno-associated virus, retrovirus, vaccinia virus and oncolytic virus. Commonly used gene transfer techniques include calcium phosphate method, DEAE-dextran method, electroporation, microinjection and viral method (Graham, F. L. and van der Eb, A. J. (1973) *Virol.* 52, 456; McCutchan, J. H. and Pagano, J. S. (1968), *J. Natl. Cancer Inst.* 41, 35 1; Chu, G., et al. (1987), *Nucl. Acids Res.* 15, 1311; Fraley, R., et al. (1980), *J. Biol. Chem.* 255, 10431; Capecchi, M. R. (1980), *Cell* 22, 479). A recently added method of introducing a nucleotide into a cell is the use of a cationic liposome (Felgner, P. L., et al. (1987), *Proc. Nati. Acad. Sci. USA* 84, 7413). Commercially available cationic lipid formulations include Tfx 50 (Promega) and Lipofectamine 2000 (Life Technologies). As a non-limiting, exemplary method for incorporating an siRNA capable of binding complementarily to the OTUB1 gene directly into a cell, lipofection may be carried out for 15-40 minutes using a mixture of 2-6 μg of cationic liposome per 1 μg of siRNA.

The pharmaceutical composition of the present invention may further include a pharmaceutically acceptable carrier or excipient. The pharmaceutically acceptable excipient is well known in the art and is a relatively inert substance that helps administration of a pharmaceutically active ingredient. For example, the excipient may impart form or viscosity or may act as a diluent. Appropriate excipients include stabilizer, wetting agent, emulsifier, salt for varying osmolarity, encapsulating agent, buffer, skin penetration enhancer, but are not limited thereto. Excipients as well as formulations for oral and parenteral drug delivery are set forth in Remington, The Science and Practice of Pharmacy, 20th ed., Mack Publishing (2000).

In another aspect, the present invention provides a method for treating cancer, including administering an effective amount of an siRNA capable of inhibiting expression of OTUB1 in a cell by complementary binding to a transcript sequence of the OTUB1 protein.

The effective amount of the siRNA is an amount sufficient to provide a desired effect, for example, decreased expression of the OTUB1 gene as compared to the expression level detected in the absence of the siRNA. The siRNA may be introduced in such an amount that at least one copy can be transferred per cell. The inhibition efficiency may be higher as the number of copies is larger (e.g., at least 5, at least 10, at least 100 or at least 1,000 copies per cell). For specific applications, a smaller introduction amount may be advantageous.

In the present invention, the term "administration" refers to introduction of a particular substance into a patient via an appropriate method. Any route of administration may be employed as long as the substance can be delivered to the target tissue. The administration route includes intraabdominal, intravenous, intramuscular, subcutaneous, intracutaneous, oral, topical, intranasal, intrapulmonary and intrarectal routes, but is not limited thereto. Also, the pharmaceutical composition may be administered using an arbitrary apparatus allowing delivery of the active ingredient to the target cell.

The "administration" means "systemic delivery" or "topical delivery" of the siRNA of the present invention to a cell expressing the OTUB1 gene. The "systemic delivery" refers to a delivery leading to a wide biodistribution in an organism. Some administration techniques may induce a systemic delivery only for specific substances. The "systemic delivery" means that an effective, specifically therapeutically effective, amount of the siRNA is exposed to the most part of the body. In general, to achieve a wide biodistribution, a long life in the blood (for example, by a primary organ (e.g., liver, lungs, etc.) or via fast non-specific binding to cells) is required which prevents the siRNA from being quickly degraded or cleared before it reaches a disease site distant from the administration site. An siRNA-lipid particle may be systemically delivered by any method known in the art, for example, intravenously, subcutaneously or intraperitoneally. In an exemplary embodiment, the siRNA particle may be systemically delivered intravenously. The "topical delivery" means a direct delivery of the siRNA to a target site in an organism. For example, the siRNA may be topically delivered to a disease site, e.g. a tumor or other target site, e.g. an inflammation site or a target organ such as the lungs, liver, heart, pancreas, kidneys, etc., by injection.

EXAMPLES

The present invention will be described in more detail through examples. The following examples are for illustrative purposes only and it will be apparent to those skilled in the art not that the scope of this invention is not limited by the examples.

Example 1

Overexpression of OTUB1 Protein in Lung Cancer Cells

Expression pattern of OTUB1 in cancer cells was investigated using WI38 normal lung cells and NCI-H358 non-small-cell lung cancer cells.

WI38 normal human lung cells and NCI-H358, NCI-H157 and A549 non-small-cell lung cancer cells were cultured in RPMI media (Gibco/BRL) containing 10% FBS (Gibco/BRL), 100 units/mL penicillin and 100 μg/mL streptomycin (Gibco/BRL) under the condition of 37° C. and 5% $CO_2$.

$2 \times 10^5$ cells were seeded onto a 6-well plate. After incubation for 24 hours, the cells were washed 3 times with cold PBS, lysed with a cell lysis buffer (50 mM Tris-Cl, pH 7.4, 150 mM NaCl, 2 mM EDTA, 0.5% NP-40, protease inhibitor cocktail, 1 mM sodium orthovanadate) and then centrifuged. After taking the supernatant, the amount of total proteins was measured using the Micro BCA protein assay kit. Proteins of the same amount were separated on SDS-PAGE gel and electrophoresed onto a nitrocellulose membrane. The membrane was then reacted with anti-OTUB1 antibodies (Bethyl Laboratories, Inc.).

As seen from FIG. 1, the expression of the OTUB1 protein was remarkably increased in the NCI-H358 non-small-cell lung cancer cells as compared to in the WI38 normal human lung cells.

Example 2

Inhibition of OTUB1 Protein Expression by siRNA siRNAs of OTUB1 were prepared and injected into NCI-H358, NCI-H157 and A549 non-small-cell lung cancer cells to investigate the inhibitory effect of the siRNA on the OTUB1 protein expression.

$2 \times 10^5$ NCI-H358, NCI-H157 and A549 non-small-cell lung cancer cells were seeded onto 6-well plates. After incubation for a day, the cells were transfected with 50 nM of the siRNAs described in Table 1 or a control siRNA (NC siRNA) (Bioneer Co., Korea) using the Lipofectamine reagent (Invitrogen). 2 days after the transfection, the inhibition of OTUB1 expression was investigated by western blotting.

TABLE 1

| | Sense | Antisense |
|---|---|---|
| siOTUB1-1 | 5'-GGUUGUAAAUGGUCCUAUU-3'<br>(SEQ ID NO 2) | 3'-CCAACAUUUACCAGGAUAA-5'<br>(SEQ ID NO 3) |
| siOTUB1-2 | 5'-CUAGACAUGUACAGAGGUU-3'<br>(SEQ ID NO 4) | 3'-GAUCUGUACAUGUCUCCAA-5'<br>(SEQ ID NO 5) |

Figure 2A:
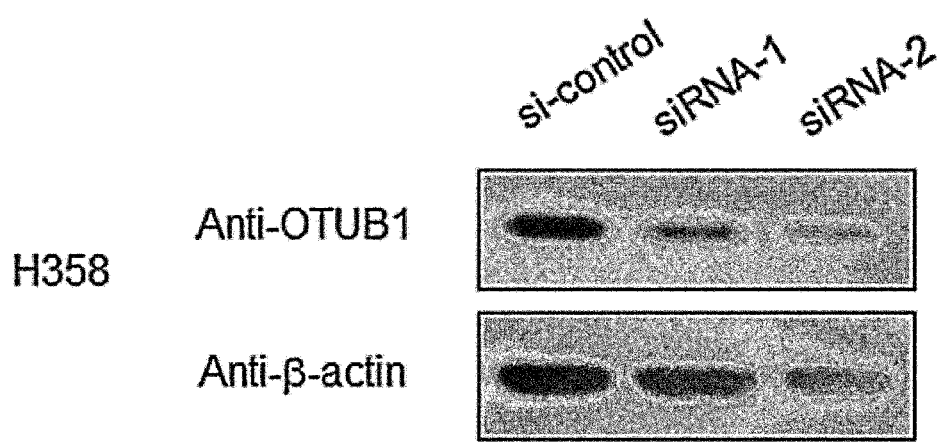
FIGS. 2a-2c show inhibited expression of the OTUB1 protein by siRNA in NCI-H358 (FIG. 2a), NCI-H157 (FIG. 2b) and A549 (FIG. 2c) non-small-cell lung cancer cells.
Figure 2B:
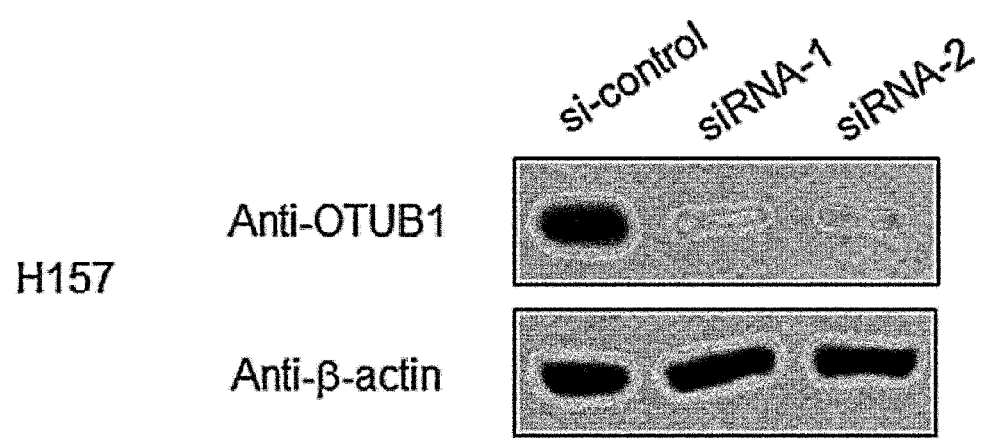
Figure 2C:
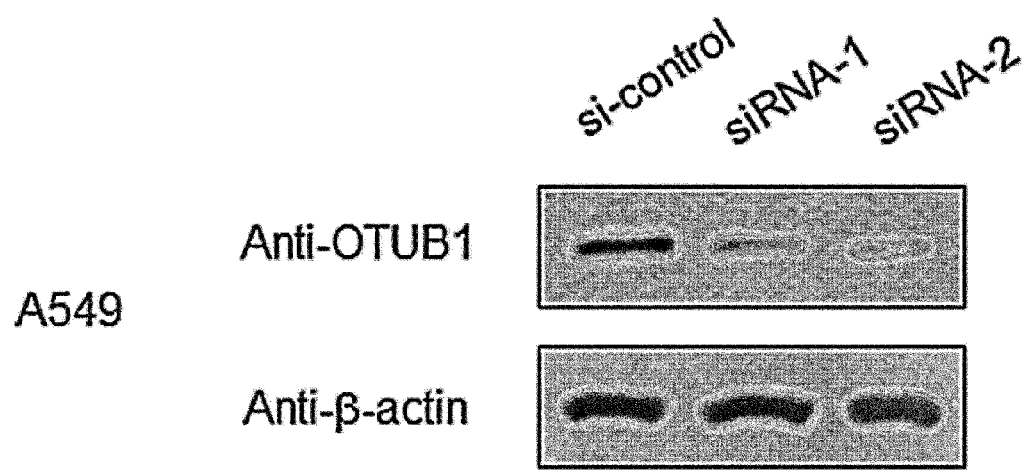

As seen from FIGS. 2a-2c, the transfection of the NCI-H358, NCI-H157 and A549 cells with OTUB1 siRNA resulted in decreased expression of OTUB1.

Example 3

Inhibition of Growth of NCI-H358, NCI-H157 and A549 Non-Small-Cell Lung Cancer Cells Through Introduction of OTUB1 siRNA The effect of introduction of OTUB1 siRNA on cell growth was investigated by WST-1 assay.

3×10³ NCI-H358, NCI-H157 and A549 non-small-cell lung cancer cells were seeded onto 6-well plates. After incubation for a day, the cells were transfected with 50 nM of the two OTUB1 siRNAs or a control siRNA (NC siRNA) (Bioneer Co., Korea) using the Lipofectamine reagent (Invitrogen) as in Example 2. 24, 48 and 72 hours after the transfection, a WST-1 solution (Daeillab Co., Korea) was added and the cells were incubated in a $CO_2$ incubator for 1 hour. Then, the effect of OTUB1 on the growth of the non-small-cell lung cancer cells was investigated by measuring absorbance at 450 nm.

Figure 3A:
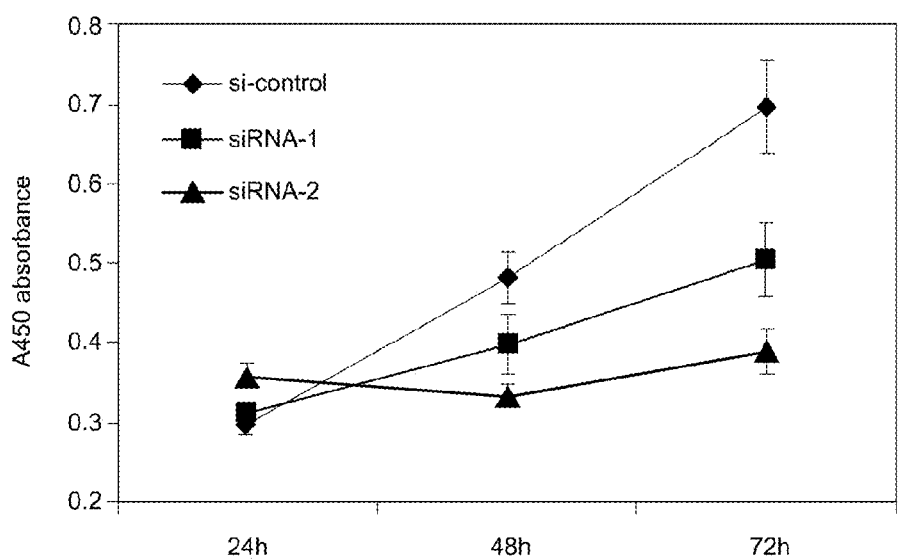
FIGS. 3a-3c show inhibited cancer cell growth of NCI-H358 (FIG. 3a), NCI-H157 (FIG. 3b) and A549 (FIG. 3c) non-small-cell lung cancer cells owing to decreased expression of the OTUB1 protein.
Figure 3B:
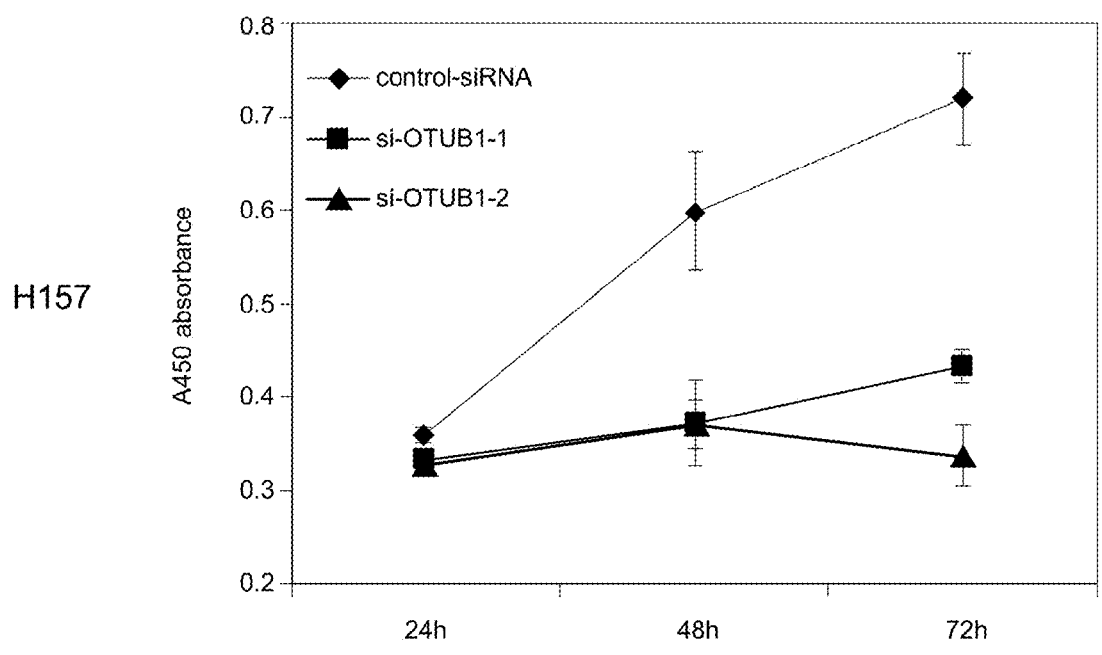
Figure 3C:
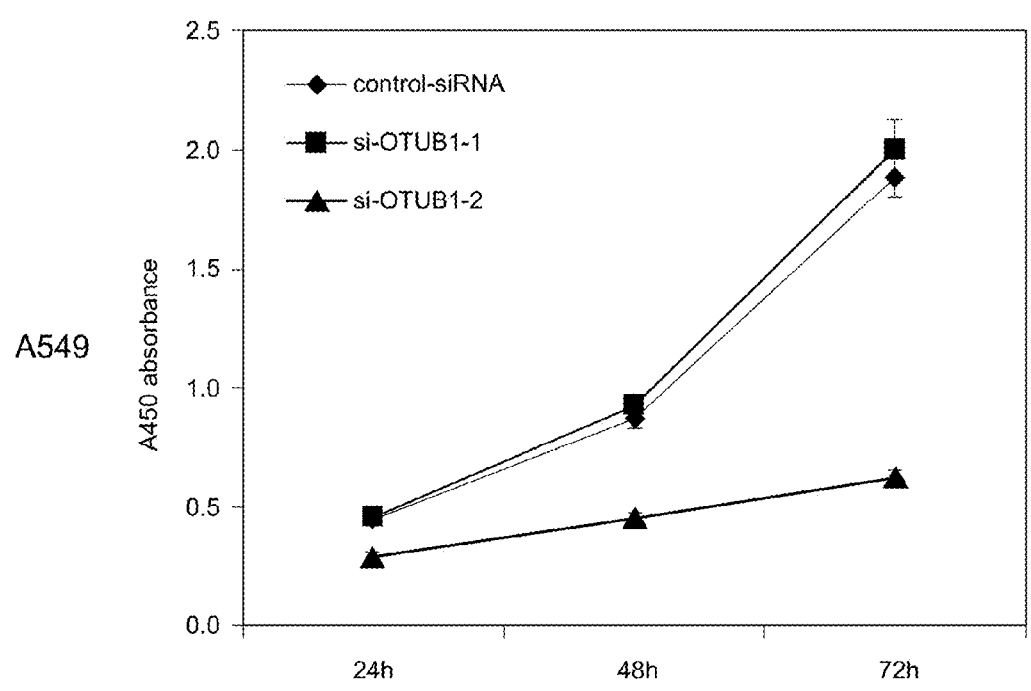

As seen from FIGS. 3a-3c, the introduction of OTUB1 siRNA resulted in decreased growth of the NCI-H358 and NCI-H157 cells. For the A549 cells, only the siRNA of SEQ ID NO 3 was effective.

Example 4

Overexpression of OTUB1 Protein Through Introduction of Flag-OTUB1 siRNA of OTUB1 was prepared and injected into WI38 normal lung cells and it was investigated whether OTUB1 was overexpressed.

2×10⁵ WI38 normal lung cells were seeded onto a 6-well plate. After incubation for a day, the cells were transfected with Flag (Sigma) and Flag-OTUB1 (Addgene) using the Lipofectamine reagent (Invitrogen). 2 days after the transfection, expression of OTUB1 was investigated by western blotting.

Figure 4:
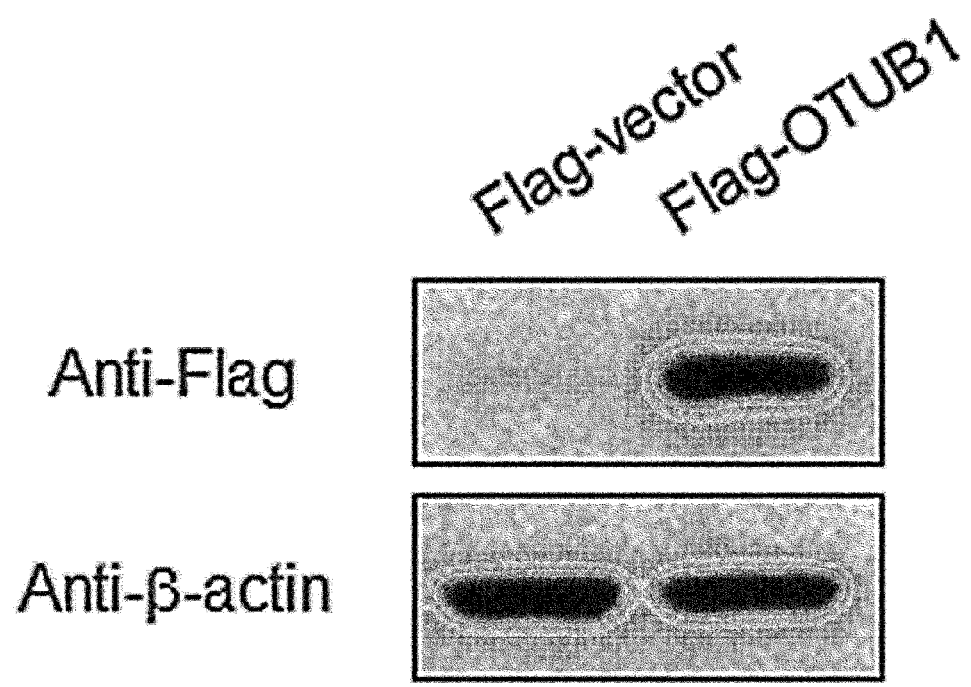
FIG. 4 shows overexpression of the OTUB1 protein in WI38 normal lung cells.

As seen from FIG. 4, the expression of Flag-OTUB1 was observed in the WI38 cells.

Example 5

Promotion of Growth of WI38 Normal Lung Cells Through Introduction of Flag-OTUB1

The effect of OTUB1 introduction on cell growth was investigated by WST-1 assay.

3×10³ WI38 normal lung cells were seeded onto a 6-well plate. After incubation for a day, the cells were transfected with Flag-OTUB1 (Bioneer Co., Korea) using the Lipofectamine reagent (Invitrogen). 24, 48 and 72 hours after the transfection, a WST-1 solution (Daeillab Co., Korea) was added and the cells were incubated in a $CO_2$ incubator for 1 hour. Then, the effect of OTUB1 on the growth of the normal lung cells was investigated by measuring absorbance at 450 nm.

Figure 5:
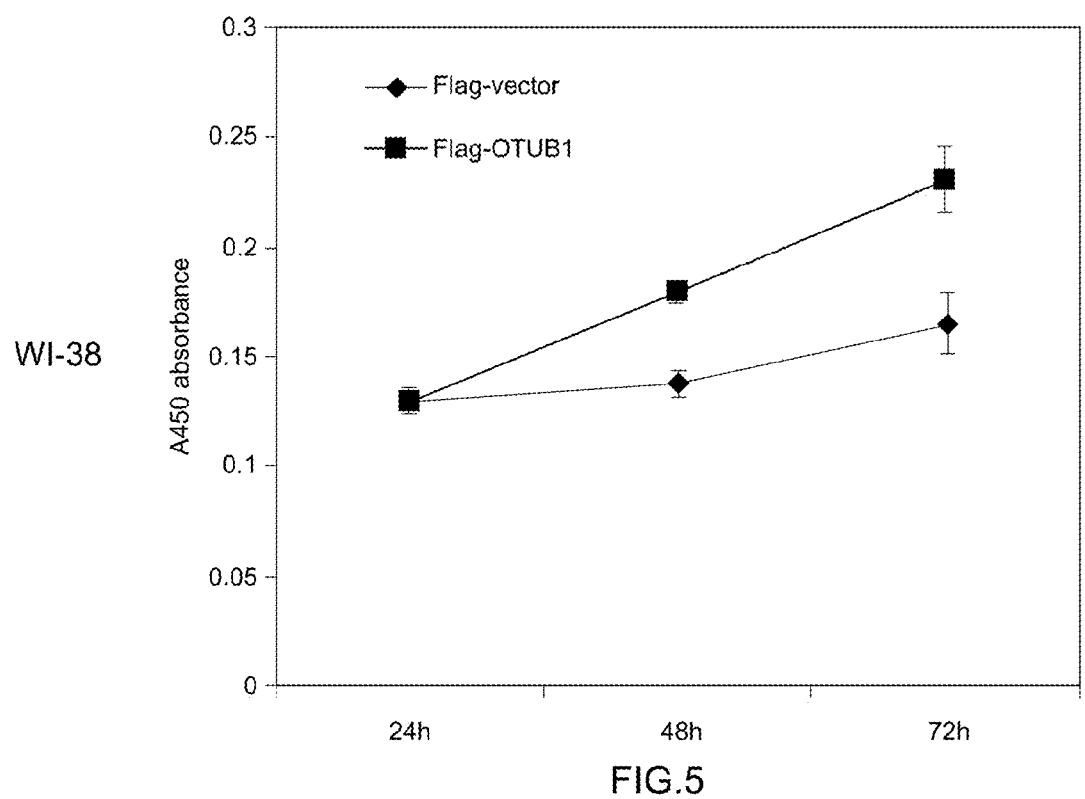
FIG. 5 shows increased cell growth of WI38 normal lung cells owing to overexpression of the OTUB1 protein.

As seen from FIG. 5, the introduction of OTUB1 resulted in increased growth of the WI38 cells.

The features and advantages of the present disclosure may be summarized as follows:

(i) The present invention provides an siRNA inhibiting expression of the OTUB1 protein.

(ii) The present invention also provides a composition for preventing or treating cancer, containing the siRNA as an active ingredient.

(iii) In accordance with the present invention, cancer cell growth can be remarkably inhibited by inhibiting OTUB1 overexpression using the siRNA of the present invention.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

---

What is claimed is:

1. A method for inhibiting cancer cell growth, comprising administrating an effective amount of a siRNA inhibiting expression of OTUB1 in a cell by complementary binding to a transcript sequence of the OTUB1 protein of SEQ ID NO: 1, wherein the siRNA comprises a sense sequence of SEQ ID NO: 4 and an antisense sequence of SEQ ID NO: 5.

2. An siRNA inhibiting expression of the OTUB1 protein, which comprises a sense sequence of SEQ ID NO 4 and an antisense sequence of SEQ ID NO 5.

3. A pharmaceutical composition, comprising the siRNA according to claim 2 as an active ingredient.

* * * * *

SEQUENCE LISTING

<160> NUMBER OF SEQ ID NOS: 5

<210> SEQ ID NO 1
<211> LENGTH: 271
<212> TYPE: PRT
<213> ORGANISM: Homo sapiens

<400> SEQUENCE: 1

```
Met Ala Ala Glu Glu Pro Gln Gln Gln Lys Gln Glu Pro Leu Gly Ser
 1               5                  10                  15

Asp Ser Glu Gly Val Asn Cys Leu Ala Tyr Asp Glu Ala Ile Met Ala
            20                  25                  30

Gln Gln Asp Arg Ile Gln Gln Glu Ile Ala Val Gln Asn Pro Leu Val
        35                  40                  45

Ser Glu Arg Leu Glu Leu Ser Val Leu Tyr Lys Glu Tyr Ala Glu Asp
    50                  55                  60

Asp Asn Ile Tyr Gln Gln Lys Ile Lys Asp Leu His Lys Lys Tyr Ser
65                  70                  75                  80

Tyr Ile Arg Lys Thr Arg Pro Asp Gly Asn Cys Phe Tyr Arg Ala Phe
                85                  90                  95

Gly Phe Ser His Leu Glu Ala Leu Leu Asp Asp Ser Lys Glu Leu Gln
            100                 105                 110

Arg Phe Lys Ala Val Ser Ala Lys Ser Lys Glu Asp Leu Val Ser Gln
        115                 120                 125
```

```
Gly Phe Thr Glu Phe Thr Ile Glu Asp Phe His Asn Thr Phe Met Asp
            130                 135                 140

Leu Ile Glu Gln Val Glu Lys Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
            180                 185                 190

Phe Ile Glu Gly Gly Arg Thr Val Lys Glu Phe Cys Gln Gln Glu Val
            195                 200                 205

Glu Pro Met Cys Lys Glu Ser Asp His Ile His Ile Ile Ala Leu Ala
            210                 215                 220

Gln Ala Leu Ser Val Ser Ile Gln Val Glu Tyr Met Asp Arg Gly Glu
225                 230                 235                 240

Gly Gly Thr Thr Asn Pro His Ile Phe Pro Glu Gly Ser Glu Pro Lys
                245                 250                 255

Val Tyr Leu Leu Tyr Arg Pro Gly His Tyr Asp Ile Leu Tyr Lys
            260                 265                 270

<210> SEQ ID NO 2
<211> LENGTH: 19
<212> TYPE: RNA
<213> ORGANISM: Artificial Sequence
<220> FEATURE:
<223> OTHER INFORMATION: siOTUB1-1 sense

<400> SEQUENCE: 2
gguuguaaau gguccuauu                                           19

<210> SEQ ID NO 3
<211> LENGTH: 19
<212> TYPE: RNA
<213> ORGANISM: Artificial Sequence
<220> FEATURE:
<223> OTHER INFORMATION: siOTUB1-1 anti-sense

<400> SEQUENCE: 3
aauaggacca uuuacaacc                                           19

<210> SEQ ID NO 4
<211> LENGTH: 19
<212> TYPE: RNA
<213> ORGANISM: Artificial Sequence
<220> FEATURE:
<223> OTHER INFORMATION: siOTUB1-2 sense

<400> SEQUENCE: 4
cuagacaugu acagagguu                                           19

<210> SEQ ID NO 5
<211> LENGTH: 19
<212> TYPE: RNA
<213> ORGANISM: Artificial Sequence
<220> FEATURE:
<223> OTHER INFORMATION: siOTUB1-2 anti-sense

<400> SEQUENCE: 5
aaccucugua caugucuag                                           19
```